United States Patent
Smith

(10) Patent No.: US 6,248,752 B1
(45) Date of Patent: Jun. 19, 2001

(54) AZABICYCLOOCTANE COMPOSITIONS AND METHODS FOR ENHANCING CHEMOTHERAPY

(76) Inventor: Charles Duane Smith, 245 Candlewyck La., Hershey, PA (US) 17033

( * ) Notice: Subject to any disclaimer, the term of this patent is extended or adjusted under 35 U.S.C. 154(b) by 0 days.

(21) Appl. No.: 09/257,829

(22) Filed: Feb. 25, 1999

Related U.S. Application Data

(60) Provisional application No. 60/076,212, filed on Feb. 27, 1998.

(51) Int. Cl.$^7$ ................................................ A61K 31/44
(52) U.S. Cl. ........................................... 514/299; 514/922
(58) Field of Search ..................................... 514/299, 922

(56) References Cited

U.S. PATENT DOCUMENTS

| | | | | |
|---|---|---|---|---|
| 4,563,464 | * | 1/1986 | Ezer et al. ............................ | 514/299 |
| 5,314,899 | * | 5/1994 | Daly et al. ............................ | 514/339 |

* cited by examiner

*Primary Examiner*—Frederick Krass

(57) ABSTRACT

The present invention relates to compositions and methods for enhancing the efficacy of therapeutic or prophylactic drugs. These compositions and methods are particularly useful to inhibit the abilities of drug transport proteins to efflux therapeutic agents from cells. Utilities of said compositions and methods include sensitizing drug resistant cells to anti-cancer agents, preventing the development of such drug resistance, enhancing the availability of therapeutic agents to the brain, testes, eyes and leukocytes, enhancing the oral bioavailability of therapeutic agents, sensitizing drug resistant infectious organisms to anti-infection agents, and preventing the development of such drug resistance.

20 Claims, No Drawings

AZABICYCLOOCTANE COMPOSITIONS AND METHODS FOR ENHANCING CHEMOTHERAPY

This application claims the benefit of provisional application Ser. No. 60/076,212 filed Feb. 27, 1998.

This invention was made with government support Grant CA64983 awarded by the United States Public Health Service. The government has certain rights in the invention.

FIELD OF THE INVENTION

The present invention relates to chemical compounds, compositions and methods useful for increasing the therapeutic efficacy of drugs. More particularly, the invention relates to compounds and compositions which inhibit the abilities of drug transport proteins to efflux therapeutic agents from cells, and to methods for using these compounds and compositions to increase the efficacy of drugs subject to such efflux.

BACKGROUND OF THE INVENTION

Eucaryotic cells possess plasma membrane-associated transport proteins which actively efflux a variety of chemical compounds from the cells (Gottesman et al., *Ann. Rev. Biochem.* 62: 385 (1993)). The purpose of these transport proteins is to protect cells from cytotoxic and/or mutagenic compounds encountered in the diet or environment. However, these transport proteins are often very effective at removing pharmaceutical agents from target cells, thereby severely restricting their therapeutic efficacy. Consequently, compounds which inhibit these transport proteins are expected to enhance the clinical utility of drugs susceptible to such transport by enhancing their accumulation in target cells.

Two transport proteins which are important in the treatment of human diseases are termed P-glycoprotein (Pgp) and multidrug resistance-associated protein (MRP). Each of these proteins is highly effective in removing a variety of compounds from eucaryotic cells, using energy released by the hydrolysis of ATP. Because of their involvement in several human diseases, further discussed below, there is great interest in developing pharmaceutical agents which will effectively inhibit the abilities of these proteins to transport drugs. Additional transport proteins have been identified more recently, including cMOAT and additional proteins related to MRP.

An important issue regarding Pgp and MRP relates to their substrate specificity. Pharmacological comparison of cells overexpressing either Pgp or MRP have demonstrated that the resistance profiles conferred by these two transporters are only partially overlapping. For example, MRP-transfected cells demonstrate greater resistance factors for vincristine, etoposide and doxorubicin, than for vinblastine and paclitaxel (Cole et al., *Cancer Res.* 54: 5901 (1994)); whereas Pgp-overexpressing cells are extremely resistant to the later two drugs (Smith et al., *Cancer* 75: 2597 (1995)). This differential pharmacology indicates the feasibility of developing selective inhibitors of these transporters, which should provide methods useful for increasing the therapeutic efficacy of many types of pharmaceutical agents.

Another significant difference between Pgp and MRP relates to their distributions in normal tissues. P-glycoprotein has been shown to be expressed by several types of secretory cells, such as capillary endothelial cells in the brain and testis, and at sites within the pancreas, kidney and liver (Leveille-Webster and Arias, *J. Membrane Biol.* 143: 89 (1995)). In contrast, the expression of MRP mRNA occurs in virtually every type of tissue (Zaman et al., *Cancer Res.* 53: 1747 (1993)). Cells altered in disease states also differentially express Pgp and MRP, indicating that selective inhibitors will be preferred as therapeutic agents.

An example of transport protein-mediated drug resistance is the phenomenon of multidrug resistance (MDR) often encountered in cancer chemotherapy (Gottesman et al., *Ann. Rev. Biochem.* 62: 385 (1993)). In this situation, the proliferation of tumor cells that are resistant to many structurally unrelated drugs often results in the failure of chemotherapy. Tumor cells from patients undergoing chemotherapy often demonstrate elevated Pgp expression, suggesting that this mechanism of MDR is clinically important (Goldstein et al., *J. Natl. Cancer Inst. USA* 81: 116 (1989)). Recent studies have indicated that MRP is expressed in a high percentage of solid tumors and leukemias. However, no differences in MRP levels were detected between normal and malignant hematopoietic cells (Abbaszadegan et al., *Cancer Res.* 54: 4676 (1994)), and MRP levels were found to be lower in some tumors than in corresponding normal tissue (Thomas et al., *Eur. J. Cancer* 30A: 1705 (1994)). Therefore, it seems that different tumors will display different patterns of expression of Pgp, MRP and, possibly, other transporters.

Another example of drug transporter-mediated resistance is encountered in the effort to deliver drugs to the central nervous system, the testes and the eye. The blood-brain barrier exists to exclude toxic agents from the brain, and largely derives from the high level of expression of Pgp by endothelial cells in the capillaries of the brain (Schinkel et al., *J. Clin. Invest.* 97: 2517 (1996)). P-glycoprotein is similarly highly expressed in capillary endothelial cells in the eye (Holash and Stewart, *Brain Res.* 629: 218 (1993)) and testes (Holash et al., *Proc. Natl. Acad. Sci. USA* 90: 11069 (1993)), restricting the uptake of many compounds by these tissues. While these systems are useful in protecting normal tissues, they also impair the delivery of therapeutic agents to these sites when such delivery may be desired. For example, Pgp in brain capillary cells impairs effective treatment of brain tumors or neurological disease by drugs which are transported by this protein. Pgp is also highly expressed in the liver, adrenal, and kidney (Lum and Gosland, *Hematol. Oncol. Clin. North Amer.* 9: 319 (1995)), tissues in which drug delivery is restricted. It is envisioned that inhibition of Pgp or other transporters will facilitate drug delivery to these sites and so enhance the effectiveness of chemotherapy. It is also envisioned that antagonists of drug transporters will be useful in suppressing the secretion of endogenous compounds, including steroid hormones and cholesterol, providing therapeutic benefit in conditions in which excessive circulating levels of these compounds promote disease states.

Another example of drug transporter-mediated resistance is encountered in the effort to orally deliver therapeutic agents. P-glycoprotein is highly expressed at the brush-border membrane of the small intestine which reduces the bioavailability of orally administered drugs subject to transport (Sparreboom et al., *Proc. Natl. Acad. Sci. USA* 94: 2013 (1997)). It is envisioned that inhibition of Pgp or other transporters will facilitate drug absorption and so enhance the effectiveness of chemotherapy.

Another example of drug transporter-mediated resistance is encountered in the effort to deliver therapeutic agents to certain leukocytes. P-glycoprotein is highly expressed by certain subtypes of lymphocytes, natural killer cells and bone marrow stem cells (Gupta and Gollapudi, *J. Clin. Immunol.* 13: 289 (1993)). This reduces the therapeutic efficacy of drugs targeting these cells, including anti-HIV compounds for the treatment of AIDS (Yusa et al., *Biochem. Biophys. Res. Com.* 169: 986 (1990)). Furthermore, the release of inflammatory cytokines and other immunomodulators appears to involve drug transporters (Salmon and Dalton, *J. Rheumatol.* 23 (suppl. 44): 97 (1996)). It is envisioned that inhibition of Pgp or other transporters will facilitate drug accumulation in these cells and so enhance the effectiveness of chemotherapy.

Organisms other than mammals also possess transport proteins similar to Pgp which have been shown to confer resistance to chemotherapeutic agents (Ullman, *J. Bioenergetics Biomembranes* 27: 77 (1995)). While the pharmacology of these transporters is not identical to that of Pgp, certain modulators are able to inhibit drug transport by both Pgp and protozoan transporters (Frappier et al., *Antimicrob. Agents Chemother.* 40: 1476 (1996)). It is envisioned that certain MDR modulators will facilitate drug accumulation in non-mammalian cells and so enhance the effectiveness of anti-infection chemotherapy.

The preceding discussion demonstrates that drug transporters are involved in determining the success of chemotherapy in a variety of disease states. While a variety of compounds have been shown to reverse transporter-mediated MDR in cell culture (i.e. act as MDR modulators), the clinical success with these agents has been unimpressive, predominantly due to the intrinsic toxicity of heretofore used modulators, and their undesired effects on the pharmacokinetics of the accompanying drugs. However, a likely cause of the failure of these agents is their lack of selectivity for different drug transporters. For example, inhibition of MRP by MDR modulators is likely to increase the uptake of cytotoxic anticancer drugs by many normal tissues, thereby producing greater untoward toxicity for the patient. Successful chemotherapy will consequently require a panel of transporter antagonists with differential selectivity for Pgp and MRP which will allow selection of the appropriate sensitizing agent.

SUMMARY OF THE INVENTION

In accordance with one aspect, the present invention provides compounds and compositions which have been discovered to increase drug efficacy, and methods of chemosensitizing drug resistant cells using such compounds and compositions.

Compounds useful in the practice of this invention include those having the following formulae, including their pharmaceutically acceptable salts:

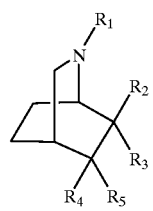

(I)

wherein $R_1$, $R_2$, $R_3$, $R_4$ and $R_5$ may be the same or different and are selected from the group consisting of —H, substituted or unsubstituted alkyl ($C_1$–$C_6$), substituted or unsubstituted alkenyl ($C_2$–$C_6$), substituted or unsubstituted aryl ($C_6$–$C_{10}$), substituted or unsubstituted aralkyl ($C_7$–$C_{11}$), halogen, haloalkyl, —OH, —O-alkyl, hydroxyalkyl, carboxy, carbalkoxy, —SH, —S-alkyl, mercaptoalkyl, —NO$_2$, and —NR'R", R' and R" being the same or different and representing H or alkyl ($C_1$–$C_6$), aryl ($C_6$–$C_{10}$) or acyl, or $R_2$ and $R_3$ together represent a carbonyl moiety (—C(=O)—), or $R_4$ and $R_5$ together with the carbon atom to which they are attached represent an alkyl substituted or unsubstituted alkylene ketal; the alkyl, alkenyl, aryl and aralkyl substituents being at least one of $R_2$, $R_3$, $R_4$ and $R_5$, as previously defined, and the phamaceutically acceptable salts thereof; or

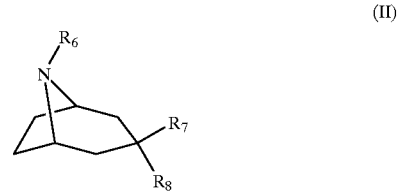

(II)

wherein $R_6$, $R_7$ and $R_8$ are the same or different and are selected from the group consisting of —H, substituted or unsubstituted alkyl ($C_1$–$C_6$), substituted or unsubstituted alkenyl ($C_2$–$C_6$), substituted or unsubstituted cycloalkyl ($C_4$–$C_{12}$), substituted or unsubstituted aryl ($C_6$–$C_{10}$), substituted or unsubstituted aralkyl ($C_7$–$C_{11}$), halogen, haloalkyl, —OH, —O-alkyl, hydroxyalkyl, hydrazino carbonyloxy, carboxy, carbalkoxy, —SH, —S-alkyl, mercaptoalkyl, —NO$_2$, and —NR$_a$R$_b$, R$_a$ and R$_b$ being the same or different and representing H or alkyl ($C_1$–$C_6$), $R_6$ additionally represents —C(=O)—O—R'", R'" representing p-chlorophenyl, and $R_7$ or $R_8$ additionally represent a N-phenyl-N-propionylamino group, and the pharmaceutically acceptable salts thereof.

Also included within the scope of this invention are isomeric forms of the above described compounds, including, without limitation, cis- and trans-isomers of the compounds of formula I, and the endo- and exo-conformations of the compounds of formula II.

The above-described compounds may be formulated into compositions with a biologically compatible vehicle or carrier for use in enhancing the therapeutic efficacy of drugs. Further these compositions may simultaneously contain an above-described compound and another transport-inhibiting compound or an additional therapeutic agent.

The present invention further provides methods for inhibiting drug transport from target cells and/or tissues, by administering an effective amount of at least one of the compounds or compositions described herein to a patient in need of such treatment.

These compounds, compositions and their use to inhibit drug transport from target cells and/or tissues are envisioned to have utility for treating MDR, including reversing MDR, chemosensitizing multidrug resistant cells to anti-cancer agents, as well as preventing MDR, by administering an effective amount of at least one of the compounds described herein to a patient in need of such treatment.

Furthermore, these compounds, compositions and their use to inhibit drug transport from target cells and/or tissues are envisioned to have utility for enhancing the delivery of therapeutic agents to the brain, testes, eye and leukocytes by administering an effective amount of at least one of the compounds described herein to a patient in need of such treatment.

Moreover, these compounds, compositions and their use to inhibit drug transport from target cells and/or tissues are envisioned to have utility for enhancing the absorption of orally-delivered therapeutic, by administering an effective amount of at least one of the compounds described herein to a patient in need of such treatment.

Additionally, these compounds, compositions and their use to inhibit drug transport from infecting organisms are envisioned to have utility for treating infectious disease, by administering an effective amount of at least one of the compounds described herein to a patient in need of such treatment.

The present invention provides a panel of novel drug transport inhibitors which include dual antagonists of Pgp and MRP, as well as transporter-selective agents. These compounds and compositions and methods for their use should provide important new therapies for a variety of disease states.

DESCRIPTION OF THE PREFERRED EMBODIMENTS

The compounds included in the foregoing summary have been found to potentiate the cytotoxicity of anticancer drugs toward drug-resistant human cancer cells. Particularly preferred are compounds of the formula:

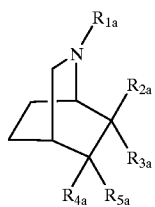

(I$_A$)

wherein $R_{1a}$ is selected from the group consisting of H, alkyl ($C_1$–$C_6$) or aralkyl ($C_7$–$C_{11}$), $R_{2a}$, $R_{3a}$, $R_{4a}$ and $R_{5a}$ may be the same or different and represent —H, —OH, —O-alkyl, —O-aralkyl, substituted or unsubstituted, straight or branched chain alkyl ($C_1$–$C_6$), substituted or unsubstituted, straight or branched chain alkenyl ($C_2$–$C_6$), or substituted or unsubstituted aryl ($C_6$–$C_{10}$), or $R_{2a}$ and $R_{3a}$ together represent a carbonyl moiety (—C(=O)—), or $R_{4a}$ and $R_{5a}$ together with the carbon atoms to which they are attached represent an alkyl substituted or unsubstituted alkylene ketal, the alkyl, alkenyl and aralkyl substituents being at least one of $R_{2a}$, $R_{3a}$, $R_{4a}$ and $R_{5a}$.

Representative examples of azabicyclo[2.2.2]octane derivatives within Formula I$_A$ include, without limitation, 2-phenethyl-5-oxo-2-azabicyclo[2.2.2]octane, 1,2-(2,2-dimethyl)propylene ketal (I-1); 2-benzyl-cis-6-hydroxy-trans-6-(3,4,5-trimethoxyphenyl)-2-azabicyclco[2.2.2]octane (I-2); 2-benzyl-6-(3,4,5-trimethoxyphenyl)-2-azabicyclo[2.2.2]octane (I-3); cis-6-(3,4,5-trimethoxyphenyl)-2-azabicyclo[2.2.2]octane (I-4); trans-6-(3,4,5-trimethoxyphenyl)-2-azabicyclo[2.2.2]octane (I-5); 2-benzyl-cis-6-hydroxy-trans-6-(3,4-dihydroxyphenyl)-2-azabicyclo[2.2.2]octane (I-6); 2-ethyl-6-anilino-2-azabicyclo[2.2.2]octane (I-7); 2-phenethyl-6-(N-propionylanilino)-2-azabicyclo[2.2.2]octane (I-8); 2-benzyl-6-trans-hydroxy-2-azabicyclo[2.2.2]octane (I-9); 2-benzyl-6-(3,4-dibenzyloxyphenyl)-6-hydroxy-2-azabicyclo[2.2.2]octane (I-10); and 5-diphenylmethylidene-2-methyl-2-azabicyclo[2.2.2]octan-6-one (I-11).

A further particularly preferred group of compounds have the formula:

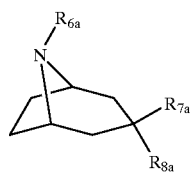

(II$_A$)

wherein $R_{6a}$ is selected from the group consisting of H, alkyl ($C_1$–$C_6$), cycloalkyl ($C_4$–$C_{12}$) or aralkyl ($C_7$–$C_{11}$), and $R_{7a}$ and $R_{8a}$ are selected from the group consisting of —H, —NR$_a$R$_b$, R$_a$ and R$_b$ being the same or different and representing H, alkyl ($C_1$–$C_6$) or hydrazinocarbonyloxy.

Representative examples of azabicyclo[3.2.1]octane derivatives within Formula II$_A$ include, without limitation, 3-hydrazinocarbonyloxy-8-(4-chlorophenoxycarbonyl)-8-azabicyclo[3.2.1]octane (II-1); 3-(N-propionylanilino)-8-phenethyl-8-azabicyclo[3.2.1]octane (II-2); 3-(N-propionylanilino)-8-benzyl-8-azabicyclo[3.2.1]octane (II-3); 3-(N-propionylanilino)-8-cyclopropylmethylene-8-azabicyclo[3.2.1]octane (II-4).

General approaches to the synthesis of azabicyclo[2.2.2]octanes and azabicyclo[3.2.1]octanes are shown below in reaction schemes 1 and 2. Cycloaddition reactions, which form the basis for synthesis of these compounds, are extremely versatile in relationship to the resultant ring systems and to their acceptance of various substituent groups.

In reaction scheme 1, a reaction, as described by Hoffman, *Angew. Chem. Int. Ed.* 12: 819 (1973), produces the [2.2.2] bicyclic ring system. Substitution of the nitrogen atom of the dihydropyridine moiety allows introduction of the $R_1$ group, whereas $R_2$ and $R_4$ substituents are easily varied through the use of substituted ethylenes, $R_1$, $R_2$ and $R_4$ as previously defined. A large number of appropriate starting materials are commercially available.

Scheme 1

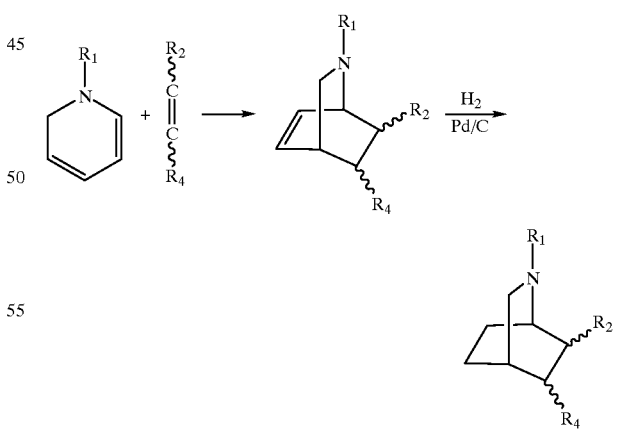

In reaction scheme 2, which is carried out according to the procedure of Hoffman, *Angew. Chem. Int. Ed.* 23: 1 (1984), heating of an N-substituted pyrrole with an allyl cation intermediate (produced by abstraction of an electron from the substituted allylhalide) produces the [3.2.1]bicyclic ring system, $R_6$ and $R_7$ as previously defined.

Scheme 2

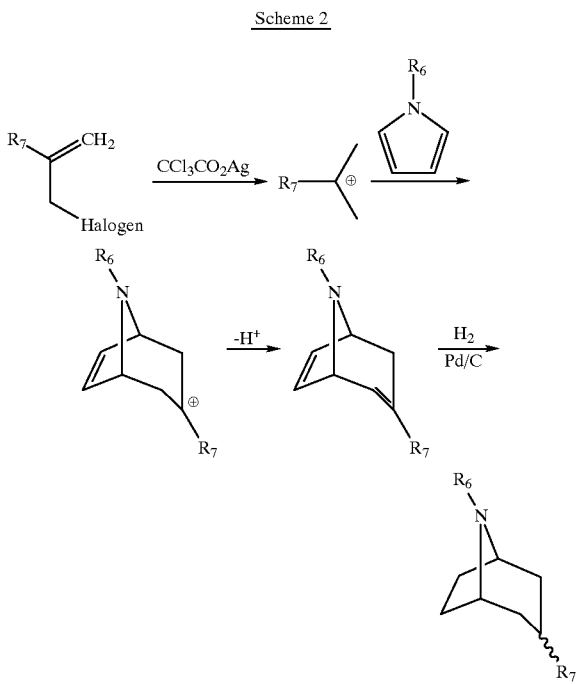

Pharmaceutically acceptable salts of the compounds described herein, which also have potentiating activity, e.g., the hydrochloride or sodium salts, may be prepared following procedures which are familiar to those skilled in the art.

The chemosensitizing pharmaceutical compositions of the present invention comprise one or more of the above-described compounds, as the active ingredient, in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein "pharmaceutically acceptable carrier medium" includes any and all solvents, diluents, or other liquid vehicle, dispersion or suspension aids, surface active agents, preservatives, solid binders, lubricants and the like, as suited to the particular dosage from desired. *Remington's Pharmaceutical Sciences*, Fifteenth Edition, E. W. Martin (Mack Publishing Co., Easton, Pa. 1975) discloses various vehicles or carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention.

In the pharmaceutical compositions of the invention, the active agent may be present in an amount of at least 1% and not more than 95% by weight, based on the total weight of the composition, including carrier medium and/or auxiliary agent(s). Preferably, the proportion of active agent varies between 1% to 70% by weight of the composition. Pharmaceutical organic or inorganic solid or liquid carrier media suitable for enteral or parenteral administration can be used to make up the composition. Gelatin, lactose, starch, magnesium, stearate, talc, vegetable and animal fats and oils, gum polyalkylene glycol, or other known excipients or diluents for medicaments may all be suitable as carrier media.

The compounds used in the practice of the invention may be administered using any amount and any route of administration effective for increasing the therapeutic efficacy of drugs. Thus the expression "therapeutically effective amount", as used herein, refers to a sufficient amount of the chemosensitizing agent to provide the desired effect against target cells. The exact amount required will vary from subject to subject, depending on the species, age, and general condition of the subject, the particular chemosensitizing agent, its mode of administration, and the like.

The therapeutic compounds described herein are preferably formulated in dosage unit form for ease of administration and uniformity of dosage. "Dosage unit form" as used herein refers to a physically discrete unit of therapeutic agent appropriate for the patient to be treated. Each dosage should contain the quantity of active material calculated to produce the desired therapeutic effect either as such, or in association with the selected pharmaceutical carrier medium. Typically, the therapeutic compound of the invention will be administered in dosage units containing from about 0.1 mg to about 10,000 mg of the agent, with a range of about 1 mg to about 1000 mg being preferred.

The compounds of the invention may be administered orally or paternally, such as by intramuscular injection, intraperitoneal injection, intravenous infusion or the like. The compounds of the invention may be administered orally or parenterally at dosage levels of about 0.1 to about 1000 mg/kg and preferably from about 1 to about 100 mg/kg, of patient body weight per day, one or more times a day, to obtain the desired therapeutic effect.

Although the compounds described herein can be administered to any subject which can benefit from their therapeutic effects, the compounds are intended particularly for the treatment of diseases in humans.

The compounds of the invention will typically be administered from 1 to 4 times a day so as to deliver the above-mentioned daily dosage. Alternatively, dosages within these ranges can be administered by constant infusion over an extended period of time, usually 1 to 96 hours, until the desired therapeutic benefits have been obtained. However, the exact regimen for administration of the compounds and compositions described herein will necessarily be dependent on the needs of the individual patient being treated, the type of treatment(s) administered and the judgment of the attending physician.

The compounds of the invention can be used in various protocols for treating patients. For example, these compounds can be used in a method for treating tumor cells in a patient requiring such treatment. This method would involve administering to a cancer patient a compound as described above in an amount effective to attenuate drug resistance in such cells.

These compounds can also be used in a method for treating hyperproliferative cells in a patient requiring such treatment, by administering the compound to a patient in an amount effective to inhibit the proliferation of said cells.

The compounds of the invention can further be used in a method for potentiating an the effectiveness of an anticancer drug in a cancer patient undergoing chemotherapy. This method would involve administering an anticancer drug and at least one compound of those described above, in an amount effective to enhance the therapeutic efficacy of the anticancer drug.

Additionally, a compound of this invention may be administered in combination with an additional compound effective to sensitize drug resistant tumor cells, the amount of the combination being effective to enhance the therapeutic efficacy of the anticancer drug. The additional compound may be selected from the group consisting of dihydropyridines, thioxanthenes, phenothiazines, cyclosporins, acridonecarboxamides, verapamil, cyclosporin A, PSC 833, tamoxifen, quinidine, quinine, bepridil, ketoconazole, megestrol acetate and estramustine. Furthermore, new agents which inhibit drug efflux are described in the literature from time to time, and these compounds are also envisioned to provide useful combinations with those of the present invention.

In view of the beneficial effect of reversal of MDR produced by the compounds of the invention, it is anticipated that these compounds will be useful not only for therapeutic treatment after the onset of MDR, but also for MDR prevention in patients about to undergo chemotherapy for the first time. The above-noted dosages will be essentially the same whether for treatment or prevention of MDR.

Similar protocols can be followed to use compounds and compositions of the present invention to enhance the therapeutic efficacy of other drugs. In view of the roles of transport proteins in impairing drug delivery to several sites within the body, these compounds and compositions will have utility in increasing drug delivery to the central nervous system, the eye, the testes, the liver, the adrenal gland, the pancreas and leukocytes. Additionally, inhibition of transport proteins in the intestine by compounds and compositions of the present invention will have utility in enhancing the bioavailability of orally delivered therapeutic agents. Furthermore, the compounds and compositions of this invention may be used to enhance the therapeutic efficacy of anti-infection drugs toward organisms which are resistant to these drugs. In each of these cases, methods would involve administering a therapeutic drug and at least one compound or composition of those described above, in an amount effective to enhance the therapeutic efficacy of the drug.

Biological studies of the above compounds as chemotherapy-enhancing agents have been performed. Inhibition of transport proteins was measured by determining the abilities of the compounds of the invention to potentiate the cytotoxicity of actinomycin D, daunomycin and/or vincristine toward cells normally resistant to these drugs. The test procedures and results of these biological studies are described below.

The following example sets forth the test protocols for evaluating the MDR reversing activity of the modulating compounds described above, along with the test results. This example is provided for illustrative purposes only, and is not intended to limit the invention.

EXAMPLE

Evaluation of Reversal of MDR Mediated by P-Glycoprotein or MRP.

The following cell lines were used in these studies: 1) MCF-7 human breast carcinoma cells; 2) MCF-7/ADR cells, an MDR subline which overexpresses Pgp (Fairchild et al. *Cancer Res.* 47: 5141 (1987) but not MRP; and 3) Human promyelocytic leukemia HL-60/ADR cells, which express MRP (Marsh et al. *Cancer Res.* 47: 4053 (1986)) but not Pgp.

To test for reversal of Pgp-mediated MDR, MCF-7/ADR cells were placed into 96-well tissue culture plates at approximately 15% confluency, and were allowed to attach and recover for 24 hr. The cells were then treated with the varying concentrations of the described compounds in the presence of 0 or 25 nM actinomycin D, or 1 µM daunomycin for 48 h according to previously described procedures (Smith et al. *Oncology Res.* 6: 211 (1994); Smith et al. *Molec. Pharm.* 47: 241 (1995)). After 48 h, cell survival was assayed using the sulforhodamine B binding assay (Skehan et al. *J. Natl. Cancer Inst. USA* 82: 1107 (1990)). The percentage of cells killed was calculated as the percentage decrease in sulforhodamine B binding compared with control cultures. Control cultures include equivalent amounts of ethanol (as the solvent control), which did not modulate the growth or drug-sensitivity of these cells at doses used in these studies. Inhibition of Pgp was manifested as the ability of the compound to potentiate the cytotoxicity of actinomycin D, daunomycin and/or vincristine toward MCF-7/ADR cells. To assess the toxicity of the compounds toward drug-sensitive cells, the effects of the test modulators on the growth of drug-sensitive MCF-7 cells were determined by the same methods.

To test for reversal of MRP-mediated MDR, HL-60/ADR cells were treated with varying concentrations of the described compounds in the presence 0 or 2 nM vincristine for 48 h. The number of surviving cells was then determined using the CellTiter™ AQ$_{ueous}$ assay system from Promega Corporation (Madison, Wis.). The percentage of cells killed was calculated as the percentage decrease in 3-(4,5-dimethylthiazol-2-yl)-5-(3-carboxymethoxyphenyl)-2-(4-sulfophenyl)-2H-tetrazolium metabolism compared with control cultures. Inhibition of MRP was manifested as the ability of the compound to potentiate the cytotoxicity of vincristine toward the HL-60/ADR cells.

The results of these tests are set forth in the following table. Chemosensitizing activity was scored on a scale of 0–5 (best activity=5), taking into account the extent of reversal and the intrinsic cytotoxicity of the compound. On this scale, compounds with activity equal or superior to verapamil score 4, 4.5 or 5. The intrinsic cytotoxicity of the compounds toward MCF-7 cells is also indicated.

| Compound | Cytotoxicity (% killed at 10 µg/ml) | Pgp antagonism | MRP antagonism |
|---|---|---|---|
| Dual antagonists | | | |
| verapamil | 15 | 4.5 | 4 |
| I-3 | 22 | 4.5 | 4 |
| I-6 | 21 | 2 | 1.5 |
| I-8 | 16 | 3 | 2.5 |
| I-11 | 8 | 4 | 4.5 |
| II-1 | 29 | 3 | 2 |
| II-2 | 19 | 3 | 3 |
| II-3 | 9 | 4.5 | 5 |
| Pgp-selective | | | |
| I-1 | 8 | 3 | 1 |
| I-7 | 26 | 4 | 1 |
| I-9 | 0 | 2 | 0 |
| I-10 | 0 | 3 | 0 |
| I-11 | 8 | 4 | 0 |
| II-4 | 17 | 3 | 0 |
| MRP-selective | | | |
| I-2 | 39 | 1 | 3 |
| I-4 | 12 | 0 | 2 |
| I-5 | 0 | 0 | 4 |

As can be seen from the foregoing test results, each compound significantly increases the toxicity of actinomycin D toward MCF-7/ADR cells and/or vincristine toward HL-60/ADR cells. The data demonstrate that the compounds are either: 1) selective inhibitors of P-glycoprotein function; 2) selective inhibitors of MRP function; or 3) dual inhibitors of both transporters. Most of the compounds tested have low intrinsic cytotoxicity, (<20% of cells killed by doses of 10 micrograms/ml).

Because of their abilities to act as selective or pleiotropic inhibitors of drug transporters, the compounds and compositions of this invention will have utility in the therapy of diseases which do not adequately respond to current chemotherapy procedures.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention.

I claim:

1. A method for inhibiting drug transport proteins in a patient undergoing chemotherapy, said method comprising administering to said patient a pharmaceutical composition comprising a compound of the formula:

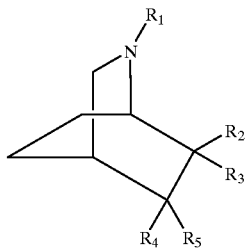

wherein $R_1$, $R_2$, $R_3$, $R_4$ and $R_5$ may be the same or different and represent H, substituted or unsubstituted alkyl ($C_1$–$C_6$), substituted or unsubstituted alkenyl ($C_2$–$C_6$), substituted or unsubstituted aryl ($C_6$–$C_{10}$), substituted or unsubstituted aralkyl ($C_7$–$C_{11}$), halogen, haloalkyl, —OH, —O-alkyl, hydroxyalkyl, carboxy, carbalkoxy, —SH, —S-alkyl, mercaptoalkyl, $NO_2$, or NR'R", R' and R" being the same or different and representing H or alkyl ($C_1$–$C_6$), aryl ($C_6$–$C_{10}$) or acyl, or $R_2$ and $R_3$ together represent a carbonyl moiety (—C(=O)—), or $R_4$ and $R_5$ together with the carbon atom to which they are attached represent an alkyl substituted or unsubstituted alkylene ketal; the alkyl, alkenyl, aryl or aralkyl substituents being at least one of $R_2$, $R_3$, $R_4$ and $R_5$, as previously defined, or the phamaceutically acceptable salts thereof in an amount effective to inhibit said drug transport proteins.

2. A method for preventing drug resistance or enhancing the therapeutic efficacy of an antiproliferative drug in a patient undergoing chemotherapy, said method comprising administering to said patient a pharmaceutical composition according to claim 1 in an amount effective to attenuate drug resistance.

3. A method for enhancing the bioavailability of a drug to the brain, the testes, the eye, or leukocytes, said method comprising administering to a patient in need thereof a pharmaceutical composition according to claim 1 in an amount effective to increase drug delivery to cells of these organs.

4. A method for enhancing the oral bioavailability of a drug, said method comprising administering to a patient in need thereof a pharmaceutical composition according to claim 1 in an amount effective to enhance said drug transport across the gastrointestinal tract.

5. A method for preventing drug resistance or enhancing the therapeutic efficacy of an anti-infective agent in a patient undergoing chemotherapy, said method comprising administering to said patient a pharmaceutical composition according to claim 1 in an amount effective to attenuate drug resistance in the infecting organism.

6. A method for inhibiting drug transport proteins in a patient undergoing chemotherapy, said method comprising administering to said patient a pharmaceutical composition comprising a compound, selected from the group consisting of: 2-phenethyl-5-oxo-2-azabicyclo[2.2.2]octane; 2-benzyl-cis-6-hydroxy-trans-6-(3,4,5-trimethoxyphenyl)-2-azabicycico[2.2.2]octane; 2-benzyl-6-(3,4,5-trimethoxyphenyl)-2-azabicyclo[2.2.2]octane; cis-6-(3,4,5-trimethoxyphenyl)-2-azabicyclo[2.2.2]octane; trans-6-(3,4,5-trimethoxyphenyl)-2-azabicyclo[2.2.2]octane; 2-benzyl-cis-6-hydroxy-trans-6-(3,4-dihydroxyphenyl)-2-azabicyclo[2.2.2]octane; 2-ethyl-6-anilino-2-azabicyclo[2.2.2]octane; 2-phenethyl-6-(N-propionylanilino)-2-azabicyclo[2.2.2]octane; 2-benzyl-6-trans-hydroxy-2-azabicyclo[2.2.2]octane; 2-benzyl-6-(3,4-dibenzyloxyphenyl)-6-hydroxy-2-azabicyclo[2.2.2]octane; and 5-diphenylmethylidene-2-methyl-2-azabicyclo[2.2.2]octan-6-one, and the pharmaceutically acceptable salts thereof in an amount effective to inhibit said drug transport proteins.

7. A method for preventing drug resistance or enhancing the therapeutic efficacy of an antiproliferative drug in a patient undergoing chemotherapy, said method cqmprising administering to said patient a pharmaceutical composition according to claim 6 in an amount effective to attenuate drug resistance.

8. A method for enhancing the bioavailability of a drug to the brain, the testes, the eye, or leukocytes, said method comprising administering to a patient in need thereof a pharmaceutical composition according to claim 6 in an amount effective to increase drug delivery to cells of these organs.

9. A method for enhancing the oral bioavailability of a drug, said method comprising administering to a patient in need thereof a pharmaceutical composition according to claim 6 in an amount effective to enhance said drug transport across the gastrointestinal tract.

10. A method for preventing drug resistance or enhancing the therapeutic efficacy of an anti-infective agent in a patient undergoing chemotherapy, said method comprising administering to said patient a pharmaceutical composition according to claim 6 in an amount effective to attenuate drug resistance in the infecting organism.

11. A method for inhibiting drug transport proteins in a patient undergoing chemotherapy, said method comprising administering to said patient a pharmaceutical composition comprising a compound of the formula:

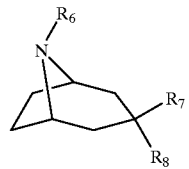

wherein $R_6$, $R_7$ and $R_8$ are the same or different and are selected from the group consisting of —H, substituted or unsubstituted alkyl ($C_1$–$C_6$), substituted or unsubstituted alkenyl ($C_2$–$C_6$), substituted or unsubstituted cycloalkyl ($C_4$–$C_{12}$), substituted or unsubstituted aryl ($C_6$–$C_{10}$), substituted or unsubstituted aralkyl ($C_7$–$C_{11}$), halogen, haloalkyl, —OH, —O-alkyl, hydroxyalkyl, hydrazino carbonyloxy, carboxy, carbalkoxy, —SH, —S-alkyl, mercaptoalkyl, —NO$_2$, and —NR$_a$R$_b$, R$_a$ and R$_b$ being the same or different and representing H or alkyl (C$_1$–C$_6$), where R$_6$ where may additionally represent —C(=O)—O-R''', R''' representing p-chlorophenyl, and R$_7$ or R$_8$ may additionally represent a N-phenyl-N-propionylamino group, or the pharmaceutically acceptable salts thereof in an amount effective to inhibit said drug transport proteins.

12. A method for preventing drug resistance or enhancing the therapeutic efficacy of an antiproliferative drug in a patient undergoing chemotherapy, said method comprising administering to said patient a pharmaceutical composition according to claim 11 in an amount effective to attenuate drug resistance.

13. A method for enhancing the bioavailability of a drug to the brain, the testes, the eye, or leukocytes, said method comprising administering to a patient in need thereof a pharmaceutical composition according to claim 11 in an amount effective to increase drug delivery to cells of these organs.

14. A method for enhancing the oral bioavailability of a drug, said method comprising administering to a patient in need thereof a pharmaceutical composition according to claim 11 in an amount effective to enhance drug transport across the gastrointestinal tract.

15. A method for preventing drug resistance or enhancing the therapeutic efficacy of an anti-infective agent in a patient undergoing chemotherapy, said method comprising administering to said patient a pharmaceutical composition according to claims 11 in an amount effective to attenuate drug resistance in the infecting organism.

16. A method for inhibiting drug transport proteins in a patient undergoing chemotherapy, said method comprising administering to said patient a pharmaceutical composition comprising a compound, selected from the group consisting of: 3-hydrazinocarbonyloxy-8-(4-chlorophenoxycarbonyl)-8-azabicyclo[3.2.1 ]octane; 3-(N-propionylanilino)-8-phenethyl-8-azabicyclo[3.2. 1 ]octane; 3-(N-propionylanilino)-8-benzyl-8-azabicyclo[3.2. 1 ]octane; 3-(N-propionylanilino)-8-cyclopropylmethylene-8-azabicyclo[3.2.1]octane; and the pharmaceutically acceptable salts thereof in an amount effective to inhibit said drug transport proteins.

17. A method for preventing drug resistance or enhancing the therapeutic efficacy of an antiproliferative drug in a patient undergoing chemotherapy, said method comprising administering to said patient a pharmaceutical composition according to claim 16 in an amount effective to attenuate drug resistance.

18. A method for enhancing the bioavailability of a drug to the brain, the testes, the eye, or leukocytes, said method comprising administering to a patient in need thereof a pharmaceutical composition according to claim 16 in an amount effective to increase drug delivery to cells of these organs.

19. A method for enhancing the oral bioavailability of a drug, said method comprising administering to a patient in need thereof a pharmaceutical composition according to claim 16 in an amount effective to enhance drug transport across the gastrointestinal tract.

20. A method for preventing drug resistance or enhancing the therapeutic efficacy of an anti-infective agent in a patient undergoing chemotherapy, said method comprising administering to said patient a pharmaceutical composition according to claim 16 in an amount effective to attenuate drug resistance in the infecting organism.

* * * * *